United States Patent [19]

Raitto

[11] 4,245,654
[45] Jan. 20, 1981

[54] BLOOD SAMPLING SYRINGE

[75] Inventor: Russell G. Raitto, Fitzwilliam, N.H.

[73] Assignee: Concord Laboratories, Inc., Keene, N.H.

[21] Appl. No.: 780,123

[22] Filed: Mar. 22, 1977

Related U.S. Application Data

[63] Continuation of Ser. No. 595,889, Jul. 14, 1975, abandoned, which is a continuation-in-part of Ser. No. 542,578, Jan. 24, 1975, abandoned.

[51] Int. Cl.$^2$ .................................................. A61B 5/00
[52] U.S. Cl. .................................... 128/765; 128/218 R
[58] Field of Search ..................... 128/2 F, 215–216, 128/218 R, 218 P, 218 PA, 218 C, 219–220, 218 D, DIG. 5, 763–766

[56] References Cited

U.S. PATENT DOCUMENTS

| | | | |
|---|---|---|---|
| 1,222,424 | 4/1917 | Laurent | 128/234 |
| 2,607,343 | 8/1952 | Sarver | 128/218 C |
| 2,756,748 | 7/1956 | Ferguson | 128/220 |
| 2,764,981 | 10/1956 | Helmer et al. | 128/218 C |
| 2,792,833 | 5/1957 | Magash et al. | 128/218 P |
| 2,856,923 | 10/1958 | Roger et al. | 128/218 P |
| 2,856,925 | 10/1959 | Helmer et al. | 128/218 C |
| 2,860,635 | 11/1958 | Wilburn | 128/218 S |
| 2,972,991 | 2/1961 | Burke | 128/218 P |
| 3,237,815 | 3/1966 | Ogle | 128/218 P |
| 3,281,023 | 10/1966 | Bruck et al. | 128/218 C X |
| 3,348,546 | 10/1967 | Roberts et al. | 128/218 R |
| 3,678,930 | 7/1972 | Schwartz | 128/218 P X |
| 3,742,949 | 7/1973 | Hill | 128/218 PA |
| 3,890,956 | 6/1975 | Moorehead | 128/2 F |
| 3,901,219 | 8/1975 | Kay | 128/2 F |
| 3,930,492 | 1/1976 | Hatsuno et al. | 128/2 F |
| 3,943,917 | 3/1976 | Johansen | 128/2 F |

FOREIGN PATENT DOCUMENTS 147466  8/1951  Australia ............................. 128/218 S

OTHER PUBLICATIONS

Albisser, A. M. et al., "Further Improvements in the Technique of Trouble-Free Blood Withdrawal", JAAMI, vol. 5, No. 4, Jul.-Aug. 1971.
Dell 'Osso, L. F. et al, "A Dual-Lumen Catheter for Continuous Blood Sampling", Med. & Biol. Engr., v. 8, #6, p. 603, 1970.

*Primary Examiner*—Robert W. Michell
*Assistant Examiner*—Francis J. Jaworski
*Attorney, Agent, or Firm*—Sewall P. Bronstein; George W. Neuner

[57] ABSTRACT

Improved disposable syringe for taking blood or other fluid samples, particularly arterial samples for blood gas testing or the like, which comprises a syringe body, a piston or plunger having a compressible end piece which forms a seal with the inner surface of the syringe body, the syringe body having a non-tapered section through which the end piece moves during withdrawal of the piston and preferably means for resisting further movement of the end piece when the desired sample size has been obtained. Also preferably the syringe has means which prevent contact between the compressible end piece and the end wall of the syringe.

16 Claims, 4 Drawing Figures

BLOOD SAMPLING SYRINGE

This is a continuation of application Ser. No. 595,889 filed July 14, 1975, now abandoned, which is a continuation-in-part of Ser. No. 542,578 filed Jan. 24, 1975, now abandoned.

BACKGROUND OF THE INVENTION

This invention related generally to hypodermic techniques for obtaining portions or samples of fluids, more particularly to a hypodermic syringe assembly for drawing blood from a patient, especially a syringe useful for drawing samples from the patient's arteries for blood gas analysis or other testing.

Various apparatus and methods for taking blood samples from patients have been previously known. Such samples are normally taken by means of a syringe which includes a cylindrical tube having a piston therein which, when pulled by an operator, creates a suction force drawing blood into the tube through a nozzle coupled to a hypodermic needle. Many of the tests are performed on blood which is obtained from the veins of the patient. However, an increasingly important method of determining the medical status of a patient is the obtaining of arterial blood samples, particularly for testing the blood for its content of various gases. Such samples are tested for the partial pressure of oxygen, the partial pressure of carbon dioxide, the pH of the blood, the electrolyte balance, and various other tests known in the art.

The syringes previously used in obtaining arterial blood samples have generally been glass syringes, in which the cylindrical body is made of glass and the piston is a ground glass rod which closely fits within the cylinder. Generally the technique for taking samples with such devices comprises a first step, the drawing of an anticoagulant solution, such as sodium heparin, into the syringe. This material also acts as a lubricant for the walls so that the glass piston may move relatively freely within the cylinder. The syringe is inverted and all air is expelled from the chamber and needle, along with the bulk of the anticoagulant solution, which is normally far in excess of the amount needed for the blood sample. It is extremely important that all air be expelled from the syringe, since one of the tests performed is the measurement of the amount of oxygen present in the blood, and even minute contamination with air will prevent accurate measurement of that amount. After suitable preparation of the patient, the hypodermic is inserted into the artery, and blood is either forced into the syringe by the pressure of the blood in the artery, or is drawn into the syringe by withdrawing the piston. One advantage of the glass syringes previously used is the ease with which the piston may be moved within the lubricated chamber. The glass piston is ground to very close tolerances, so that it is sufficiently close to the syringe wall to prevent leakage, but sufficiently far away to allow formation of a thin film of the anticoagulant. Even very low blood pressures are usually sufficient to enter the syringe and force the glass piston backwards without any aid from the person taking the sample. Upon entry into the syringe the blood mixes with whatever anticoagulant solution remained in the needle and tip of the syringe after the excess had been expelled.

The glass syringes previously used have suffered from a number of disadvantages. They are expensive, since the grinding requires close tolerances, in the order of 0.0007 inches clearance between the piston and the cylindrical syringe body. They are easily breakable, which is especially costly after the sample has been taken. The glass piston and the glass barrel of each syringe must commonly be matched during the grinding by the manufacturer, since variations in grinding from one piston to another may be sufficient to permit leakage of air or other material around the piston, which will contaminate the sample. Thus the cylinders and pistons cannot easily be individually mass produced, since the pistons often cannot be satisfactorily interchanged one with another in any given cylinder, as pointed out in U.S. Pat. No. 2,419,401 to Hinds. Further, because of the easy movement of the glass plunger in the cylinder, the plunger falls out of the cylinder of its own weight, and normally breaks on the floor, unless the syringe is carried needle end down. Special metal holders for the glass cylinder have been used to prevent this problem.

Attempts have been made to avoid these disadvantages by either manufacturing both the cylinder and the piston out of materials other than glass, such as plastics, or by using glass cylinders with plastic plungers or pistons. However, these attempts have not produced an acceptable product. In order to prevent leakage around the piston, these devices depend upon the use of a compressible tip on the end of the piston adjacent the hypodermic needle, which tip generally has a number of ribs which are larger than the inside diameter of the cylinder in their uncompressed state and which, when placed within the cylinder, are compressed against the interior wall of the cylinder and form a seal. This type of seal, however, with the materials previously used, has made the movement of the piston within the cylinder more difficult, thus normally requiring manual withdrawal of the piston to obtain the blood sample. The handling of the syringe which is involved when manual withdrawal of the piston is required may cause traumatization or collapse of the artery from which the blood is being taken. A further major problem has been the fact that when pressure is applied to expel the excess anticoagulant solution, the compressible tip on the end of the piston compresses and deforms against the end of the cylinder. When the piston is released prior to the insertion of the hypodermic needle into the artery, the pressure on the compressible tip is also released, which causes the piston to move back slightly, drawing a small amount of air into the tip of the hypodermic needle. Since the samples which are drawn to test for the amount of oxygen and carbon dioxide in the blood, are very small, e.g., 2, 5 or 10 ml, even minute amounts of oxygen leaked into the sample have potentially adverse affects on the results obtained. The compressibility of the plunger tip also causes non-uniformity in the amount of anticoagulant left in the tip of the syringe and hypodermic needle. As can be readily appreciated, the amount left will depend upon the amount of pressure used to expel the oxygen and excess anticoagulant, since greater pressure will compress or distort the compressible plunger tip to a greater degree, thus expelling more anticoagulant. If too little anticoagulant solution remains to be mixed with the blood, the blood may coagulate prior to testing and thus adversely affect the results obtained. If, on the other hand, too much anticoagulant solution is left in the syringe, its presence will also adversely affect the test, as is known in the art.

Accordingly, an object of the present invention is to provide a simple, inexpensive blood sampling syringe, particularly one suitable for taking arterial blood samples, which avoids the difficulties previously encountered with the glass syringes used for such purposes, and yet avoids any contamination of the sample which will interfere with the results obtained. It is a further object of the invention to provide such a syringe which is adapted to prevent air being sucked into the hypodermic needle when the plunger is released prior to taking the sample. It is a further object of the invention to provide such a syringe which is adapted so as to supply a uniform amount of anticoagulant solution to the blood sample being taken. It is a further object to provide such a syringe having an easily movable piston whereby the possibility of traumatization of the patient is minimized. It is a still further object to provide such a syringe which limits the amount of sample taken to a precise, predetermined amount, and which allows easy movement of the piston and a uniform seal throughout the distance travelled by the piston to obtain that amount of sample. It is a further object to provide a syringe having all of these advantages which is simple and inexpensive to manufacture, and thus of low cost to the patient, and extremely simple to operate in a manner which gives uniform and representative results.

Other objects and advantages of the present invention will be apparent from a reading of the present specification, or from the practice of the invention herein disclosed.

SUMMARY OF THE INVENTION

Briefly, the above advantages are obtained in accordance with the present invention by providing a syringe in which at least a portion of the cylinder has a constant inside diameter, i.e. the inside walls of the cylinder do not taper inward or outward. Preferably, the non-tapered portion of the cylinder extends over the distance through which the compressible end piece on the piston must travel in taking the sample. More preferably, the cylinder has a non-tapered portion at the needle end of the syringe, the size or length of which is predetermined depending on the size of sample desired, and the cylinder is also provided with a stop which resists movement of the compressible end piece beyond the point where the desired sample size has been obtained.

This invention is particularly useful in combination with the invention described in my copending application Ser. No. 542,578, filed Jan. 24, 1975, which disclosed a syringe in which the compressible end piece is prevented from contacting the end of the cylindrical body adjacent the hypodermic needle. This is preferably accomplished by providing a stoppage means on the piston which contacts the other end of the cylindrical syringe body at a point whereby the movement of the piston is stopped prior to contacting the end of the syringe. In this manner, the compressible tip which forms a seal between the cylinder and the piston cannot be compressed against the end of the cylindrical chamber which bears the hypodermic needle and thus cannot force the piston to withdraw slightly upon being released from compression, and draw air into the tip of the needle. Similarly, the amount of anticoagulant solution supplied to the blood using the syringe of the present invention is very uniform from sample to sample, since the same amount is retained in the space left when the plunger or piston is fully inserted, no matter how much pressure is applied to the piston. Preferably, the compressible tip of the piston is also adapted to minimize friction between the piston and the inside of the cylindrical body, while maintaining an adequate seal.

For a better understanding of the invention, reference is made to the following detailed descriptions to be read in conjunction with the accompanying drawing, in which FIG. 1 is a planar side view of the preferred syringe of the present invention;

Figure 1:
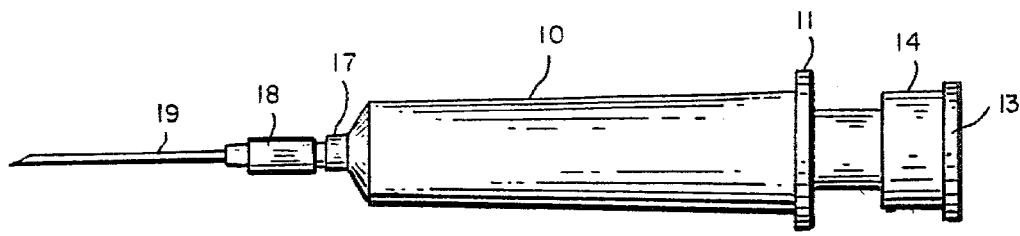
Figure 2:
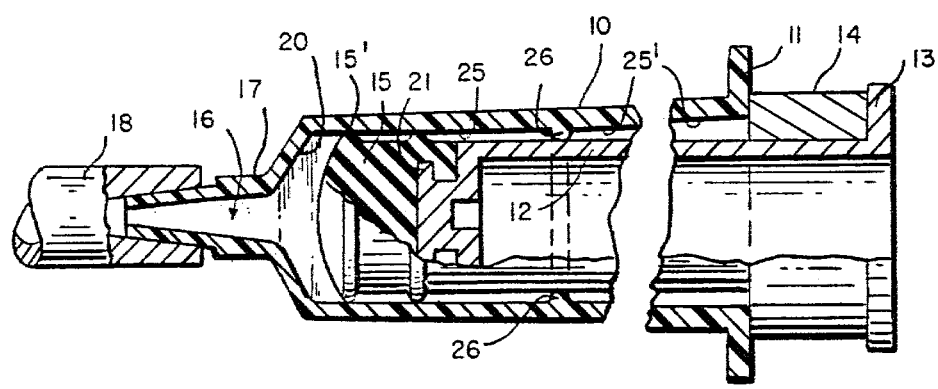
FIG. 2 is a longitudinal section of the syringe of FIG. 1.

Referring to FIGS. 1 and 2 of the drawing, the syringe depicted has a cylindrical body or tube 10, preferably made of an inexpensive substantially transparent plastic material, such as polyethylene or polypropylene, which is inert to, i.e. does not effect, the sample to be taken, and which is substantially impermeable to oxygen and carbon dioxide. Other suitable materials, such as polystyrenes, acryllic or methacryllic polymers, and various glasses, are well known in the art. The cylindrical tube terminates at one end with finger piece 11. This piece is generally annular but can be any shape which provides support for two fingers, e.g. hexagonal, or taking the form of two tabs. The tube terminates at the other end in a tube wall 20 which bears an open tip 16 of reduced size. As shown, tip 16 is generally frustoconical, opening toward the cylindrical body 10. Tip 16 carries the hypodermic needle 19 through frictional engagement with cylindrical connecting member 18. As shown, tip 16 also bears an annular ring 17, which aids in the proper placement of the hypodermic needle on the syringe by limiting the distance up the tip to which connector 18 may be pushed.

The syringe also comprises a plunger or piston denoted generally at 12. At the outside end, this piston terminates in a thumb support surfaces shown as annular surface 13. The plunger terminates at the other end in a protrusion 21 which engages compressible end piece 15 having ridges 15' abutting the inside surface of cylindrical body 10.

Figures 3, 4:
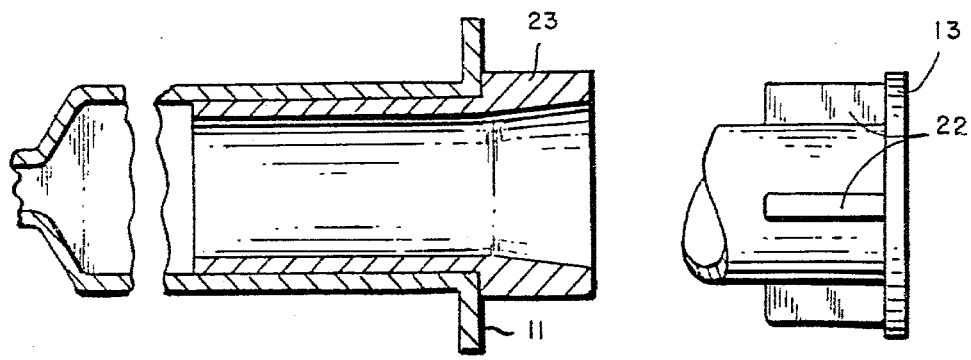
FIG. 3 shows an alternative embodiment of means for stopping the motion of the piston.
FIG. 4 shows another alternative embodiment of means for stopping the motion of the piston.

The syringe depicted in FIG. 2 has means 14 for limiting the inward motion of the piston so that end piece 15 does not come into contact with the inner end 20 of the cylindrical body 10. As shown in FIGS. 1 and 2, that means comprises an annular ring, which is preferably frictionally or otherwise attached to the outer end of piston 12 adjacent to thumb support area 13. The limiting means, however, can take other shapes or forms, such as one or a plurality of limiting bars or protrusions 22 circumferentially spaced around the outside of the piston adjacent the thumb support area, as shown in FIG. 3. The limiting means may be separate means which are attached to the outside of the piston, or may be molded or otherwise formed as part of the piston itself. Another embodiment is shown in FIG. 4, where the limiting means comprises cylindrical member 23, which has a thin cylindrical portion inserted into the syringe tube, and a thicker shoulder portion which extends around the open end of the tube and arrests the inward motion of the plunger. This embodiment has several advantages, in that it can be simply snapped in place in standard syringe tubes, and it can be made in such proportions that the thin cylindrical portion within the tube not only holds the element in place, it also tends to stop the outward motion of the plunger when the proper blood sample size has been reached.

The size of the limiting means is preferably fixed so that when the inward motion of the plunger is stopped the space between the inner end of compressible end piece 15 and the inner end of the cylindrical body 10 is such that the amount of anticoagulant solution contained in that space, and in the free space within tip 16, connector 18 and hypodermic needle 19, is the proper amount to be mixed with the blood sample desired. Preferably, this amount of anticoagulant solution is between about 0.01 and 1.0 milliliters, more preferably between about 0.25 and 0.5 milliliters, for every five milliliters of blood sample desired. Most preferably the amount of anticoagulant left in the syringe is from about 0.3 to 0.4 milliliter per five milliliters of blood sample to be taken.

Compressible end piece 15 is designed to minimize the amount of friction between it and the inner surface of the cylindrical syringe body 10, while at the same time insuring that no air or other material is allowed to seep by the edges of the piston and thus contaminate the sample. As shown, the compressible end piece bears two ridges 15' which engage the inner surface of the cylindrical body. The end piece may have as few as one or as many as desired of such ridges, provided that the aforementioned functions are served. In the preferred embodiment the compressible end piece 15 is made out of compressible material having a low coefficient of friction with the material which makes up the inside of the syringe body. Silicone rubbers are most preferred, but other elastomeric materials such as natural or synthetic rubber, such as neoprene rubber, and other compressible plastics, such as polyvinyl chlorides, urethanes, polyesters, etc., known in the art, are suitable.

In fashioning plastic syringes, it has been the practice to mold the cylindrical syringe barrel with a slight taper, i.e. with the walls of the barrel converging slightly toward the end of the barrel bearing the hypodermic needle. This is normally done because in injection molding the barrel with polyethylene or other plastic it is necessary to have such a taper in order to facilitate the removal of the syringe barrel from the mold. However, in accordance with the present invention, it has been found that a substantial improvement results in the operation of the syringe which results from avoiding the taper present in previous plastic syringes. Because of the constant cross-sectional area of the cylinder encountered as the compressible end piece 15 is drawn through the barrel, the amount of compression exerted on the compressible end piece remains constant. In turn, the frictional force exerted on the end piece as it passes over the barrel walls, which depends to some degree on the force exerted on those walls because of the compression of the end piece, tends also to remain constant throughout the movement of the piston. By contrast, previously known tapered plastic syringes start the piston or plunger withdrawal with the compressible end piece at the narrowest part of the neck, with compression and thus frictional forces at a maximum. The compression decreases as the piston is withdrawn in these tapered syringes, but the compression must be sufficient to avoid leakage throughout the working area of the syringe. As can easily be seen, since the compression has to be sufficient at the end of the withdrawal stroke to maintain a seal, the compression, and thus the frictional resistance to movement, is highest at the start of the withdrawal of the sample and can be far higher than the minimum amount necessary to form an adequate seal. This is precisely the opposite from the conditions desired in drawing arterial blood samples, since difficulty in withdrawing the samples can easily result in traumatization or collapse of the artery. Ideally, the arterial blood pressure should be sufficient to force the blood into the syringe, in order to avoid any need for manual withdrawal of the piston with the attendant danger of collapsing the artery.

In the present invention, compression is not maximized at the point where the sample withdrawal begins. Rather, the diameter of the working area of the barrel and the size, shape and composition of the compressible end piece can be designed so that the minimal compression necessary to get an effective seal is exerted on the compressible end piece, and this minimal compression will be the same throughout the working area. Thus, the blood pressure does not have to overcome the greatest frictional resistance to start the movement of the plunger and work against unnecessarily higher friction than necessary to keep it moving. Rather, the blood pressure need only overcome the standing and sliding frictional forces caused by the minimal compression needed for an adequate seal. Moreover, if the arterial blood pressure is not sufficient to force the piston back, and the piston therefore has to be withdrawn manually, the present invention is still beneficial, since the uniform force required to withdraw the piston promotes easy regulation of the withdrawal rate and resulting avoidance of trauma to the artery by abrupt and uneven withdrawal of fluid.

In accordance with the present invention, the inside walls 25 of the cylinder are non-tapered in at least the working area, i.e. the area of the cylinder which is traversed by the piston end piece in taking the sample. Thus, as shown in FIG. 2, the side walls of the cylinder are straight in the longitudinal direction and there is no convergence of divergence in the area 25 between the closet approach of end piece 15 to end wall 20, and annular rib 26, which serves to resist further outward movement of the end piece 15 when the sample of a desired size has been drawn into the syringe. The area of the cylinder beyond the working area of the end piece (e.g. the area designated 25' to the right of rib or ridge 26 in FIG. 2) may be tapered or not, as desired. Of course, the flexibility of the end piece permits movement of the piston beyond rib 26 if desired, and also permits easy assembly of the disposable syringe by simply pushing the piston into the cylinder until it snaps over rib 26. More than one rib 26 can be provided to allow the syringe to accommodate different sample sizes and as the sample is being taken each rib will not only serve as a means for obtaining extremely precise sample sizes, but also will serve as a check, since each time the plunger stops at a rib the person taking the sample can easily see whether the desired sample size has been reached. Rib 26 as shown is substantially semicircular, so as to avoid injury to the compressible end piece during assembly or use of the syringe, but such ribs can be of other shapes or sizes. Where the sample must be transferred from the syringe for analysis, the rib or ribs should be placed at the points where the desired volume of sample will be expelled when the plunger is pushed in fully. As will be understood, some material will remain in the space left inside the needle, the tip and the space between the innermost reach of the piston and the end wall of the syringe.

As indicated above, a frictional fitting for connector 18 is shown in FIGS. 1 and 2, but other fittings are well known and are suitable, possibly even more suitable in certain circumstances. The most commonly used fitting for such sampling syringes is the luer lock fitting, in which the connecting element 18 has tabs, usually two in number, annularly displaced around the edge of the connector which is to be connected to the syringe. These tabs fit into a generally cylindrical fitting located on tip 16, the inside surface of which is threaded. The needle in this case is attached to the syringe simply by inserting the tab end of connector 18 into the fitting and screwing it on tightly. The luer lock fitting is generally preferred, albeit more expensive.

As will be readily appreciated, the problems experienced with prior blood sampling syringes are largely eliminated by the present invention. Because of the limiting member which prevents the compression of the compressible end piece of the piston against the inner end wall of the cylindrical syringe body, no air is taken into the hypodermic needle after the expulsion of the air and excess anticoagulating solution, since the end piece is not allowed to compress against the inner end of the cylindrical tube and thus create a suction when pressure is released from the end of the piston. Similarly, the limitation is to the distance of travel allows standard syringes to be made with highly uniform volumes remaining after full insertion of the piston, thus giving uniform and accurate amounts of anticoagulant solution to be mixed with the blood sample, from one syringe to another. The tolerances on that are not nearly as high as in the case of the glass syringes, and all parts can be cheaply mass produced out of inexpensive raw materials. There is no breakage problem and the system is sufficiently simple and inexpensive to make the entire syringe disposable after the sample is analyzed or transferred to other equipment. Thus where a comparative series of tests are being run on a patient, for example, each syringe may be disposed of as soon as the test sample is transferred from the syringe to the testing equipment and each syringe when fully depressed will contain the same amount of the anticoagulant material. This insures that the samples will not coagulate or deteriorate between the time that they are taken from the patient and analyzed, and that too much anticoagulant will not be present in the blood sample as analyzed.

While the present syringe is particularly suitable for taking arterial blood samples, its suitability for other functions will be readily appreciated in the art. The syringe of the present invention is disposable and sufficiently inexpensive that it can be made readily available throughout the whole hospital. In using it there is no blood sample loss on account of breakage of the glass syringe after it has been filled with the sample.

The above constitutes a disclosure of the preferred embodiments of the present invention, but it will be apparent and appreciated by those skilled in the art that many changes and modifications may be made therein without departing from the essential spirit of the invention, which is indicated in the following claims.

I claim:

1. A disposable plastic syringe assembly for obtaining blood samples, comprising:
   a substantially cylindrical tube having an open end, a partially closed end, an opening extending through said partially closed end, and conduit means for conveying a sample from a source, through said opening and into said tube;
   a piston slidably mounted within said tube having a first end protruding from said open end of said tube and a second end disposed within said tube, and a compressible end piece mounted on the second end of said piston and adapted to form a slidable seal with the inside wall of the tube;
   said substantially cylindrical tube, having a nontapered section for holding the sample, and an annularly tapered section extending from said open end to the midsection region of the tube said tube being uniform in inside diameter throughout the length of said nontapered section, and said non-tapered section being located between the partially closed end of said tube and the tapered section.

2. A disposable plastic syringe assembly for obtaining an arterial blood sample from a patient, comprising:
   a substantially cylindrical tube forming a barrel having a central bore, an open end, a partially closed end forming a floor of the barrel, an opening extending through said partially closed end, and a syringe tip having a needle secured thereto and conduit means therethrough for conveying a sample of blood from said patient, through said needle and opening into said barrel when said needle is inserted into a blood vessel of said patient;
   A plunger slidably mounted within said bore having a first end protruding from said open end of said barrel and a second end disposed within said bore and a compressible plunger tip mounted on the second end of said plunger in frictional compression with respect to the wall of said bore to form a slidable seal with said wall;
   said barrel being of molded plastic and said bore having a nontapered working section normally traversed by the plunger tip in taking said sample, and an annularly tapered section extending from the end of the nontapered section located in the midsection region of the barrel to the open end of the barrel, said nontapered section being uniform in diameter throughout its length and being located between the partially closed end of said barrel and the tapered section so that the frictional sealing force on said plunger tip by said wall of said bore is substantially uniform in drawing said sample, said frictional sealing force being sufficiently small so that the pressure of said patient's blood when said needle is inserted into a blood vessel of said patient is adequate to move said plunger axially in said barrel away from said floor to draw said sample into said barrel.

3. The syringe assembly of claim 2, said wall of said bore further comprising an annular rib at about the intersection of said nontapered and tapered sections.

4. A disposable plastic syringe assembly for obtaining an arterial blood sample from a patient comprising:
   a substantially cylindrical tube forming a barrel having a central bore, an open end, a partially closed end forming the floor of said bore, an opening extending through said partially closed end, and a syringe tip having a needle secured thereto and conduit means therethrough for conveying a sample of blood from said patient through said needle and opening into said barrel when said needle is inserted into a blood vessel of said patient;
   a plunger slidably mounted within said bore having a first end protruding from said open end of said barrel and a second end disposed within said bore, and a compressible plunger tip mounted on the second end of said plunger in frictional compression with respect to the wall of said bore to form a slidable seal with said wall and having an end face forming with said partially closed end of said tube a chamber which varies in size with sliding movement of said piston in said tube;

said barrel being of molded plastic and said bore being uniform in diameter throughout its length between the partially closed end and the location of said compressible plunger tip in the midsection region of the barrel when said blood sample has been drawn so that the frictional sealing force on said plunger tip by said wall is substantially uniform in drawing said sample, and being annularly tapered throughout its length from said location of said compressible end piece in said midsection region to said open end, and means for limiting the minimum size of said chamber formed by inward movement of said piston toward said floor, said frictional sealing force being sufficiently small so that the pressure of said patient's blood when said needle is inserted into a blood vessel of said patient is adequate to move said plunger axially in said barrel away from said floor to said location to draw said sample into said barrel.

5. The syringe assembly of claim 4, said wall of said bore having an annular rib located at about the intersection of said uniform diameter length and said tapered length.

6. The syringe assembly of claim 4, wherein said limiting means comprises an annular ring attached to said piston adjacent said first end thereof.

7. The syringe assembly of claim 4, wherein said limiting means comprises at least one protrusion on said piston adjacent said first end thereof.

8. The syringe assembly of claim 4, wherein said limiting means stops the inward movement of said plunger at a point where the volume remaining in said syringe and said needle is from about 0.05 to 0.5 milliliter for each five milliliters of blood sample to be analyzed.

9. The syringe assembly of claim 8, wherein said limiting means limits the inward movement of said plunger at a point where the column remaining in said syringe and said needle is from about 0.3 to 0.4 milliliter for each five milliliters of blood sample to be analyzed.

10. The syringe assembly of claim 2, wherein said compressible end piece comprises a silicone rubber.

11. The syringe assembly of claim 2, wherein said cylindrical barrel comprises a material selected from the group of polyethylene, polypropylene, and polystyrene.

12. A method of taking a blood sample from a patient and mixing it with an anticoagulant, comprising withdrawing an anticoagulant from a source into a syringe having a molded plastic barrel having a bore, a needle cannula, a plunger for axial movement in said bore and having a compressible tip in compressive sealing engagement with the wall of said bore and means to limit the inward movement of the plunger to establish a minimum free volume in the barrel, said bore being uniform in diameter throughout its length between the partially closed end and the location of said compressible plunger tip when said blood sample has been drawn so that the frictional sealing force on said plunger tip by said wall is substantially uniform in drawing said sample, and being annularly tapered throughout its length from said location of said compressible end piece to said open end, expelling from said syringe air and anticoagulant in excess of an amount which is sufficient to prevent coagulation in the blood sample to be taken but is less than the amount which will adversely affect the test to be performed, said air and excess anticoagulant being expelled by moving said plunger into the barrel to the innermost limit allowed by said limiting means, and thereafter inserting the needle into a blood vessel of a patient and allowing the blood pressure of the patient to force a predetermined amount of the blood sample into the barrel and thereby move the plunger outwardly until said predetermined amount is drawn into said barrel stopping with the compressible end piece remaining in the uniform diameter section of the bore, whereby the blood sample mixes with the anticoagulant left in said syringe.

13. The method of claim 12, wherein the volume of anticoagulant left in the syringe after expulsion is from about 0.3 to 0.4 milliliter for each five milliliters of blood sample to be taken.

14. The method of claim 13, wherein the size of the blood sample taken is limited by a means on the inside surface of said syringe for stopping the outward motion of the plunger.

15. A method according to claim 12, the compressive sealing force on said compressible tip by said bore wall being substantially uniform during said outward movement of said plunger to draw said sample.

16. A method of taking a blood sample and mixing it with an anticoagulant, comprising withdrawing an anticoagulant from a source into a syringe having a molded plastic barrel having a bore, a needle cannula, a plunger for axial movement in said bore and having a compressible tip in compressive sealing engagement with the wall of said bore, said bore being uniform in diameter throughout its length between the partially closed end and the location of said compressible plunger tip when said blood sample has been drawn so that the frictional sealing force on said plunger tip by said wall is substantially uniform in drawing said sample, and being annularly tapered throughout its length from said location of said compressible end piece to said open end, expelling from said syringe air and excess anticoagulant over a predetermined amount thereof by moving said plunger into the barrel and thereafter inserting the needle into a blood vessel of a patient and allowing the blood pressure of the patient to force a predetermined amount of the blood sample into the barrel and thereby move the plunger outwardly until said predetermined amount is drawn into said barrel stopping with the compressible end piece remaining in the uniform diameter section of the bore, whereby the blood sample mixes with the anticoagulant left in said syringe, the compressive sealing force on said compressible tip by said bore wall resisting the force of said blood pressure on said plunger being substantially uniform during said outward movement of said plunger to draw said sample.

* * * * *